US008500778B2

United States Patent
Jackson et al.

(10) Patent No.: US 8,500,778 B2
(45) Date of Patent: Aug. 6, 2013

(54) INTERSPINOUS PROCESS SPACER

(75) Inventors: Benjamin L. Jackson, Chadds Ford, PA (US); David Chow, West Chester, PA (US); Robert J. Delurio, Aston, PA (US)

(73) Assignee: Depuy Synthes Products, LLC, Raynham, MA (US)

( * ) Notice: Subject to any disclaimer, the term of this patent is extended or adjusted under 35 U.S.C. 154(b) by 525 days.

(21) Appl. No.: 12/162,939

(22) PCT Filed: Jan. 31, 2007

(86) PCT No.: PCT/US2007/002791
§ 371 (c)(1),
(2), (4) Date: Dec. 29, 2008

(87) PCT Pub. No.: WO2007/089905
PCT Pub. Date: Aug. 9, 2007

(65) Prior Publication Data
US 2009/0306715 A1 Dec. 10, 2009

Related U.S. Application Data
(60) Provisional application No. 60/764,069, filed on Feb. 1, 2006.

(51) Int. Cl.
*A61B 17/70* (2006.01)
(52) U.S. Cl.
USPC .......................................... 606/249
(58) Field of Classification Search
USPC ..................... 606/247–249; 623/17.11–17.16
See application file for complete search history.

(56) References Cited

U.S. PATENT DOCUMENTS
4,298,993 A * 11/1981 Kovaleva et al. .......... 623/22.36
4,904,261 A * 2/1990 Dove et al. ................. 623/17.16
(Continued)

FOREIGN PATENT DOCUMENTS
| EP | 1330987 | 7/2003 |
| EP | 1 334 703 | 8/2003 |

(Continued)

OTHER PUBLICATIONS
International Search Report, completed Jul. 31, 2007 for International Application No. PCT/US2007/002791, filed Jan. 31, 2007.

(Continued)

*Primary Examiner* — Eduardo C. Robert
*Assistant Examiner* — Mary Hoffman
(74) *Attorney, Agent, or Firm* — Meunier Carlin & Curfman, LLC

(57) ABSTRACT
An interspinous process spacer is generally rectangular and may have an upper face that generally opposes a lower face, front and back sides that generally oppose each other, an end side, and a nose that generally opposes the end side. The spacer preferably has rounded edges between the upper face and the front, end, and back sides and between the lower face and the front, end, and back sides. The nose of the spacer is preferably asymmetrical and tapers integrally, distally, and inwardly from the first and second faces to form a generally pointed or rounded distal tip. A spacer may be inserted laterally into the interspinous space through a small, posterior midline incision, allowing the preservation of the supraspinous ligament. One or more spacers may be placed between spinous processes of adjacent vertebrae, and result in distraction of the spinous processes which may limit extension of the spine.

18 Claims, 12 Drawing Sheets

U.S. PATENT DOCUMENTS

| | | | | |
|---|---|---|---|---|
| 4,917,704 | A * | 4/1990 | Frey et al. | 623/17.16 |
| 5,011,484 | A * | 4/1991 | Breard | 606/249 |
| 5,059,193 | A | 10/1991 | Kuslich | 606/61 |
| 5,496,318 | A | 3/1996 | Howland et al. | 606/61 |
| 5,836,948 | A * | 11/1998 | Zucherman et al. | 606/249 |
| 5,980,572 | A * | 11/1999 | Kim et al. | 623/17.16 |
| 6,111,164 | A * | 8/2000 | Rainey et al. | 623/16.11 |
| 6,235,030 | B1 | 5/2001 | Zucherman et al. | 606/61 |
| 6,261,586 | B1 * | 7/2001 | McKay | 424/423 |
| 6,332,882 | B1 | 12/2001 | Zucherman et al. | 606/61 |
| 6,332,883 | B1 | 12/2001 | Zucherman et al. | 606/61 |
| 6,419,676 | B1 | 7/2002 | Zucherman et al. | 606/61 |
| 6,451,019 | B1 | 9/2002 | Zucherman et al. | 606/61 |
| 6,500,177 | B1 | 12/2002 | Martinelli et al. | 606/57 |
| 6,579,318 | B2 * | 6/2003 | Varga et al. | 623/17.11 |
| 6,613,090 | B2 * | 9/2003 | Fuss et al. | 623/17.11 |
| 6,626,944 | B1 * | 9/2003 | Taylor | 623/17.16 |
| 6,652,527 | B2 | 11/2003 | Zucherman et al. | 606/61 |
| 6,695,842 | B2 | 2/2004 | Zucherman et al. | 606/61 |
| 6,699,246 | B2 | 3/2004 | Zucherman et al. | 606/61 |
| 6,699,247 | B2 | 3/2004 | Zucherman et al. | 606/61 |
| 6,699,288 | B2 * | 3/2004 | Moret | 623/17.16 |
| 6,733,534 | B2 | 5/2004 | Sherman | 623/17.16 |
| 6,749,636 | B2 * | 6/2004 | Michelson | 623/17.16 |
| 6,761,720 | B1 * | 7/2004 | Senegas | 606/249 |
| 6,949,123 | B2 * | 9/2005 | Reiley | 623/17.11 |
| 6,974,480 | B2 * | 12/2005 | Messerli et al. | 623/17.16 |
| 7,018,413 | B2 * | 3/2006 | Kruger | 623/17.11 |
| 7,029,473 | B2 | 4/2006 | Zucherman et al. | 606/61 |
| 7,048,762 | B1 * | 5/2006 | Sander et al. | 623/17.11 |
| 7,060,073 | B2 * | 6/2006 | Frey et al. | 606/85 |
| 7,060,096 | B1 * | 6/2006 | Schopf et al. | 623/17.11 |
| 7,137,997 | B2 * | 11/2006 | Paul | 623/17.11 |
| 7,201,751 | B2 | 4/2007 | Zucherman et al. | 606/61 |
| 7,479,160 | B2 * | 1/2009 | Branch et al. | 623/17.11 |
| 7,686,832 | B2 * | 3/2010 | Jackson | 606/249 |
| 7,771,456 | B2 * | 8/2010 | Hartmann et al. | 606/249 |
| D625,821 | S * | 10/2010 | Goncalves et al. | D24/155 |
| 7,837,688 | B2 * | 11/2010 | Boyer et al. | 606/86 A |
| 7,879,109 | B2 * | 2/2011 | Borden et al. | 623/23.76 |
| 7,892,261 | B2 * | 2/2011 | Bonutti | 606/279 |
| 8,034,079 | B2 * | 10/2011 | Bruneau et al. | 606/249 |
| 8,070,777 | B2 * | 12/2011 | Soboleski et al. | 606/247 |
| 8,070,778 | B2 * | 12/2011 | Zucherman et al. | 606/248 |
| 8,147,554 | B2 * | 4/2012 | Hansell et al. | 623/17.16 |
| 2001/0012938 | A1 * | 8/2001 | Zucherman et al. | 606/61 |
| 2002/0029039 | A1 * | 3/2002 | Zucherman et al. | 606/61 |
| 2003/0093153 | A1 * | 5/2003 | Banick et al. | 623/17.11 |
| 2004/0162616 | A1 * | 8/2004 | Simonton et al. | 623/17.11 |
| 2004/0186572 | A1 * | 9/2004 | Lange et al. | 623/17.11 |
| 2004/0210222 | A1 * | 10/2004 | Angelucci et al. | 606/69 |
| 2004/0220568 | A1 | 11/2004 | Zucherman et al. | 606/61 |
| 2005/0027360 | A1 * | 2/2005 | Webb et al. | 623/17.11 |
| 2005/0055031 | A1 | 3/2005 | Lim | 606/99 |
| 2005/0090829 | A1 * | 4/2005 | Martz et al. | 606/79 |
| 2005/0143738 | A1 | 6/2005 | Zucherman et al. | 606/61 |
| 2005/0177238 | A1 * | 8/2005 | Khandkar et al. | 623/17.11 |
| 2005/0187625 | A1 * | 8/2005 | Wolek et al. | 623/17.11 |
| 2005/0203512 | A1 | 9/2005 | Hawkins et al. | 606/61 |
| 2005/0203624 | A1 | 9/2005 | Serhan et al. | 623/17.11 |
| 2005/0209603 | A1 | 9/2005 | Zucherman et al. | 606/90 |
| 2005/0228383 | A1 | 10/2005 | Zucherman et al. | 606/61 |
| 2005/0261768 | A1 | 11/2005 | Trieu | 623/17.11 |
| 2006/0084988 | A1 | 4/2006 | Kim | 606/61 |
| 2006/0085069 | A1 | 4/2006 | Kim | 623/17.11 |
| 2006/0085070 | A1 | 4/2006 | Kim | 623/17.11 |
| 2006/0129243 | A1 * | 6/2006 | Wong et al. | 623/17.16 |
| 2006/0184247 | A1 | 8/2006 | Edidin et al. | 623/17.11 |
| 2006/0184248 | A1 | 8/2006 | Edidin et al. | 623/17.11 |
| 2006/0224159 | A1 * | 10/2006 | Anderson | 606/61 |
| 2006/0235532 | A1 * | 10/2006 | Meunier et al. | 623/17.16 |
| 2006/0241601 | A1 | 10/2006 | Trautwein et al. | 606/61 |
| 2006/0241613 | A1 * | 10/2006 | Bruneau et al. | 606/69 |
| 2006/0247623 | A1 * | 11/2006 | Anderson et al. | 606/61 |
| 2006/0247634 | A1 * | 11/2006 | Warner et al. | 606/61 |
| 2006/0264938 | A1 | 11/2006 | Zucherman et al. | 606/61 |
| 2006/0271049 | A1 | 11/2006 | Zucherman et al. | 606/61 |
| 2006/0271194 | A1 * | 11/2006 | Zucherman et al. | 623/17.11 |
| 2006/0293662 | A1 * | 12/2006 | Boyer et al. | 606/61 |
| 2006/0293663 | A1 * | 12/2006 | Walkenhorst et al. | 606/61 |
| 2007/0010813 | A1 | 1/2007 | Zucherman et al. | 606/61 |
| 2007/0043361 | A1 | 2/2007 | Malandain et al. | 606/61 |
| 2007/0043362 | A1 | 2/2007 | Malandain et al. | 606/61 |
| 2007/0043363 | A1 | 2/2007 | Malandain et al. | 606/61 |
| 2007/0049934 | A1 | 3/2007 | Edidin et al. | 606/61 |
| 2007/0049935 | A1 | 3/2007 | Edidin et al. | 606/61 |
| 2007/0055237 | A1 | 3/2007 | Edidin et al. | 606/61 |
| 2007/0055373 | A1 * | 3/2007 | Hudgins et al. | 623/17.11 |
| 2007/0093830 | A1 | 4/2007 | Zucherman et al. | 606/61 |
| 2007/0129804 | A1 * | 6/2007 | Bentley et al. | 623/17.11 |
| 2007/0149972 | A1 * | 6/2007 | Nakajima et al. | 606/61 |
| 2007/0173832 | A1 | 7/2007 | Tebbe et al. | 606/61 |
| 2007/0203493 | A1 | 8/2007 | Zucherman et al. | 606/61 |
| 2007/0203497 | A1 | 8/2007 | Zucherman et al. | 606/61 |
| 2007/0203501 | A1 | 8/2007 | Zucherman et al. | 606/61 |
| 2007/0208347 | A1 | 9/2007 | Zucherman et al. | 606/61 |
| 2007/0219552 | A1 | 9/2007 | Zucherman et al. | 606/61 |
| 2007/0225706 | A1 | 9/2007 | Clark et al. | 606/61 |
| 2007/0270951 | A1 * | 11/2007 | Davis et al. | 623/17.11 |
| 2007/0270963 | A1 * | 11/2007 | Melkent et al. | 623/17.11 |
| 2008/0021562 | A1 * | 1/2008 | Huppert | 623/17.16 |
| 2008/0058937 | A1 * | 3/2008 | Malandain et al. | 623/17.11 |
| 2008/0065219 | A1 * | 3/2008 | Dye | 623/17.16 |
| 2008/0077247 | A1 * | 3/2008 | Murillo et al. | 623/17.16 |
| 2008/0154377 | A1 * | 6/2008 | Voellmicke | 623/17.16 |
| 2008/0249622 | A1 * | 10/2008 | Gray | 623/17.11 |
| 2008/0269904 | A1 * | 10/2008 | Voorhies | 623/17.16 |
| 2008/0294263 | A1 * | 11/2008 | Altarac et al. | 623/17.16 |
| 2008/0312695 | A1 * | 12/2008 | Sybert et al. | 606/263 |
| 2008/0312741 | A1 * | 12/2008 | Lee et al. | 623/17.11 |
| 2009/0248076 | A1 * | 10/2009 | Reynolds et al. | 606/246 |
| 2009/0265008 | A1 * | 10/2009 | Thibodeau | 623/17.16 |
| 2010/0057130 | A1 * | 3/2010 | Yue | 606/249 |
| 2010/0198263 | A1 * | 8/2010 | Siegal et al. | 606/279 |
| 2010/0211102 | A1 * | 8/2010 | Belliard et al. | 606/249 |
| 2010/0241166 | A1 * | 9/2010 | Dwyer et al. | 606/249 |
| 2010/0256760 | A1 * | 10/2010 | Hansell | 623/17.11 |
| 2011/0022091 | A1 * | 1/2011 | Anderson et al. | 606/249 |
| 2012/0165942 | A1 * | 6/2012 | Khanna | 623/17.16 |

FOREIGN PATENT DOCUMENTS

| | | |
|---|---|---|
| FR | 2 722 980 | 2/1996 |
| WO | WO 02/07624 | 1/2002 |
| WO | WO 03/007791 | 1/2003 |
| WO | WO 2005/009300 | 2/2005 |
| WO | WO 2006/064356 | 6/2006 |

OTHER PUBLICATIONS

International Preliminary Report on Patentability dated Aug. 5, 2008.

* cited by examiner

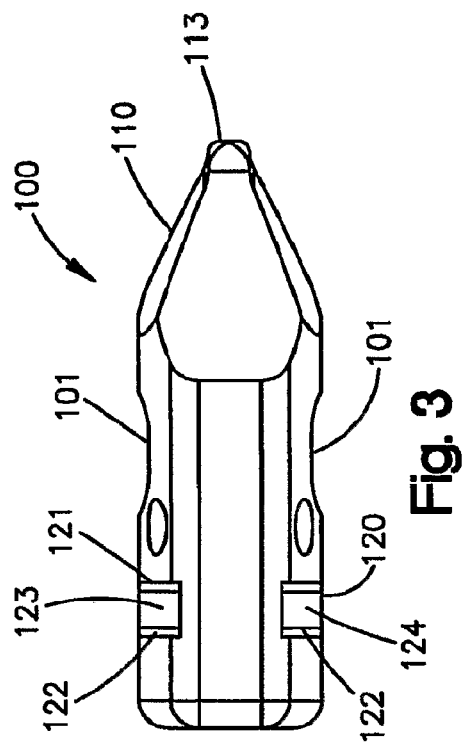
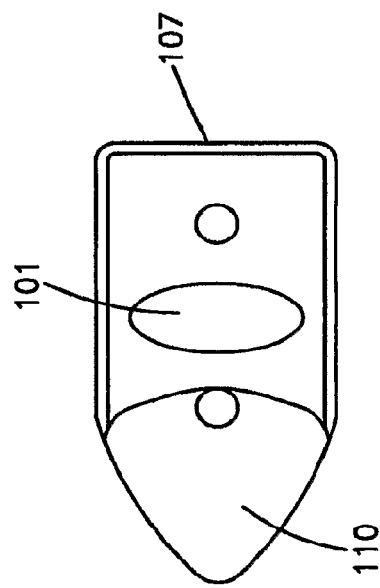
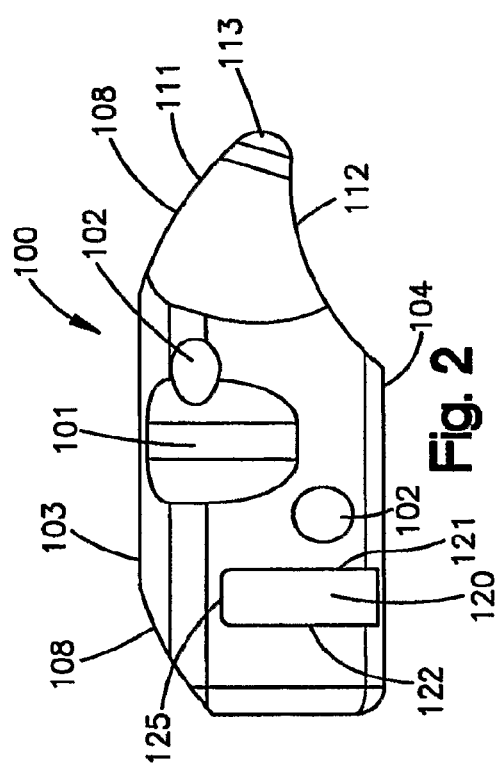
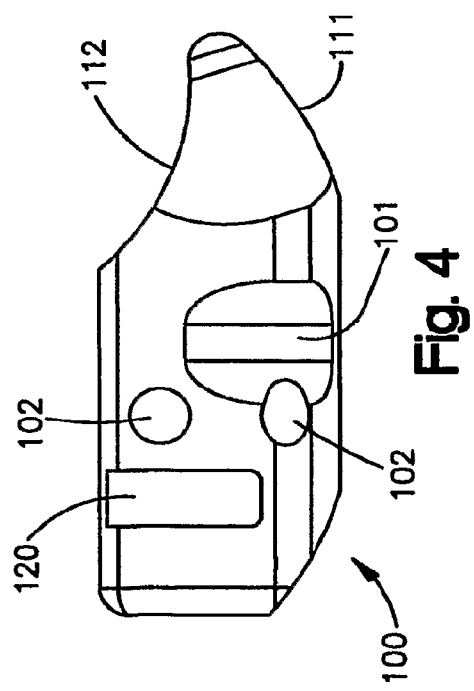

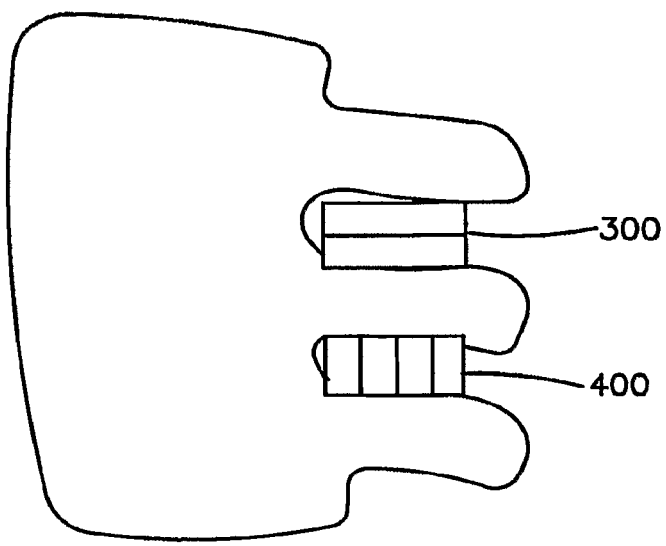
Fig. 11
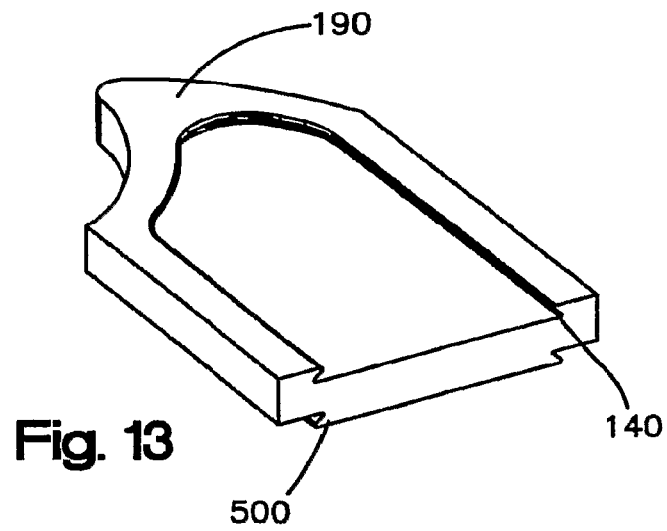
Fig. 12
Fig. 13

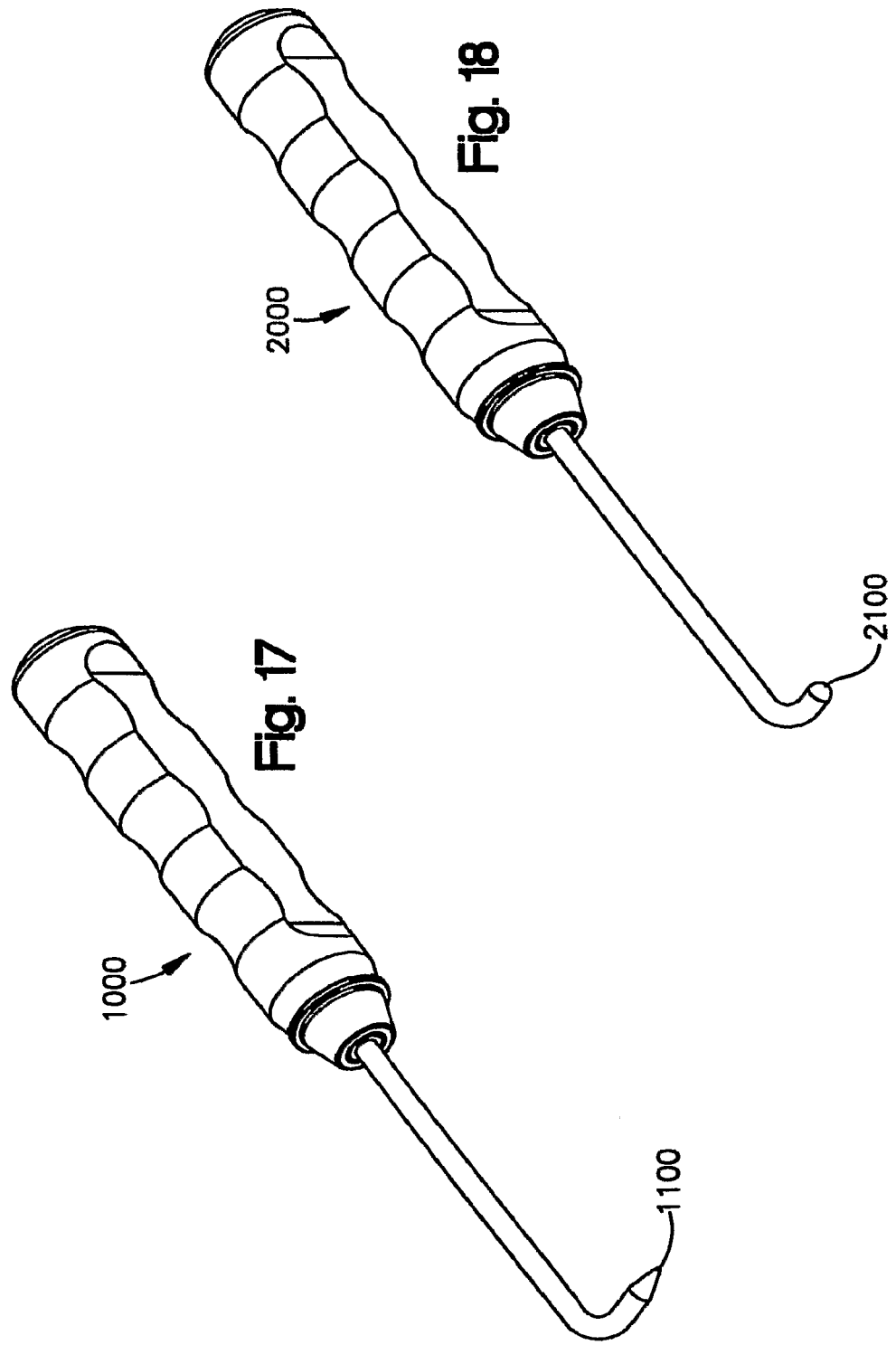

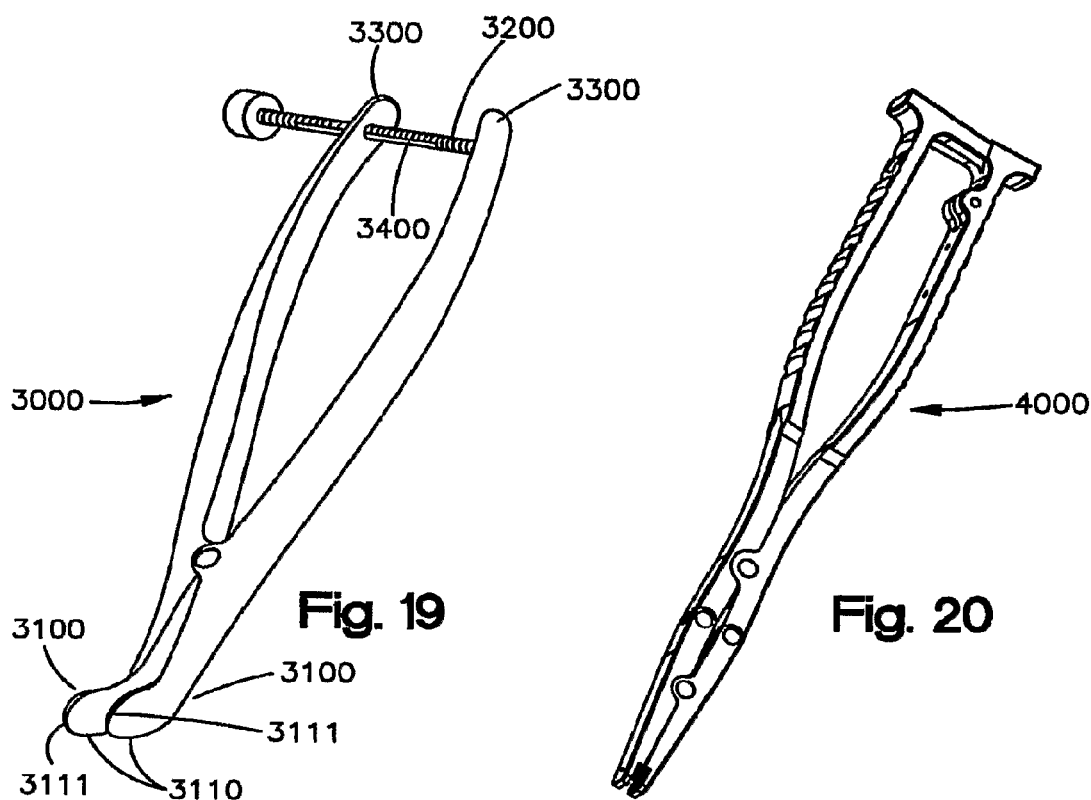
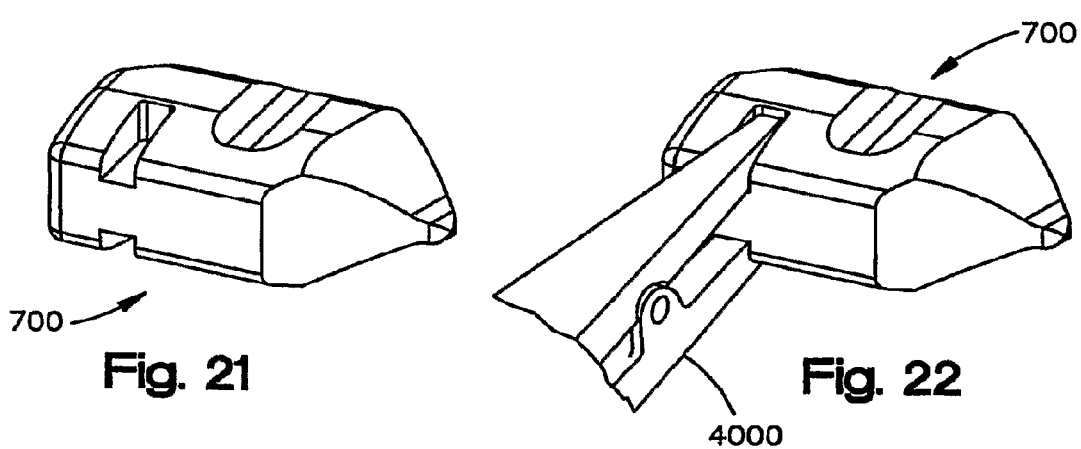

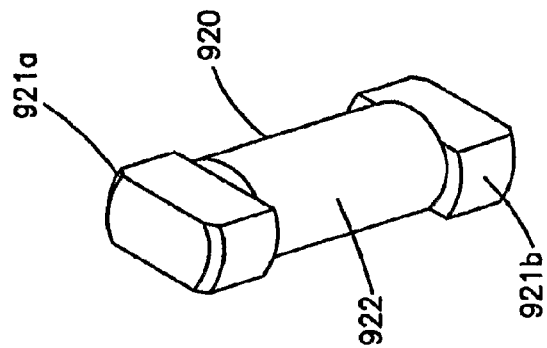
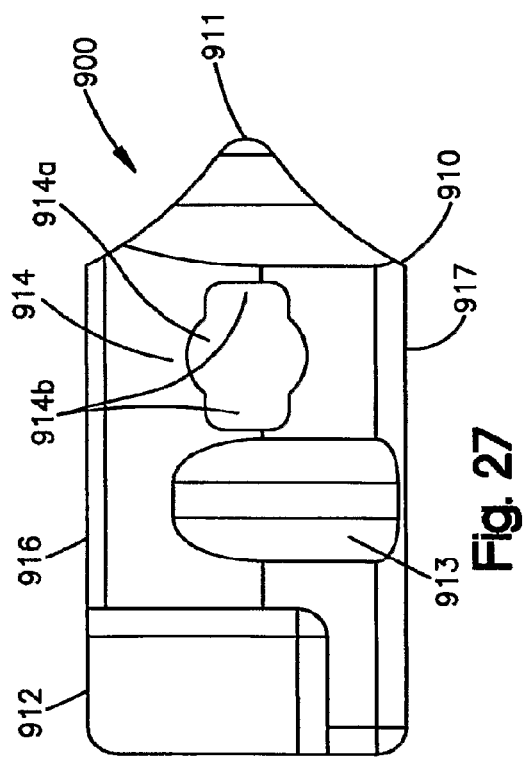
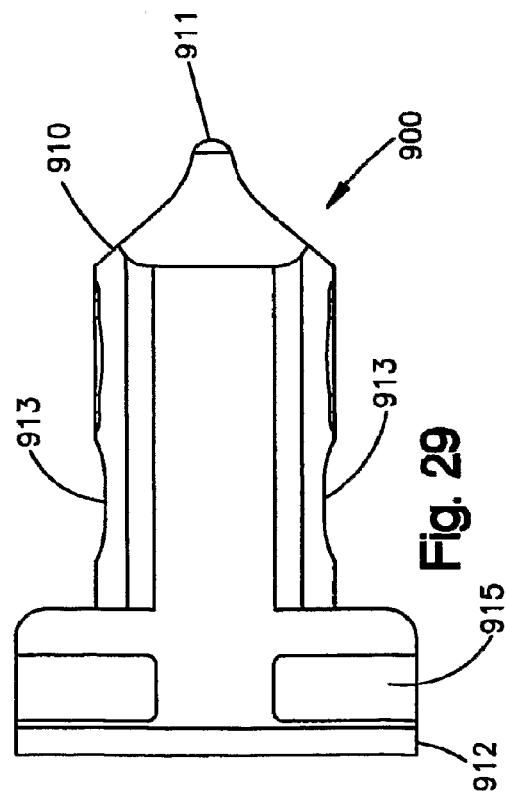

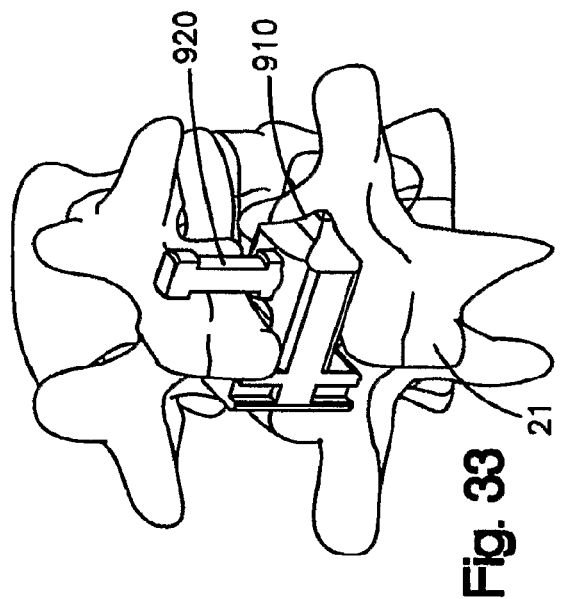
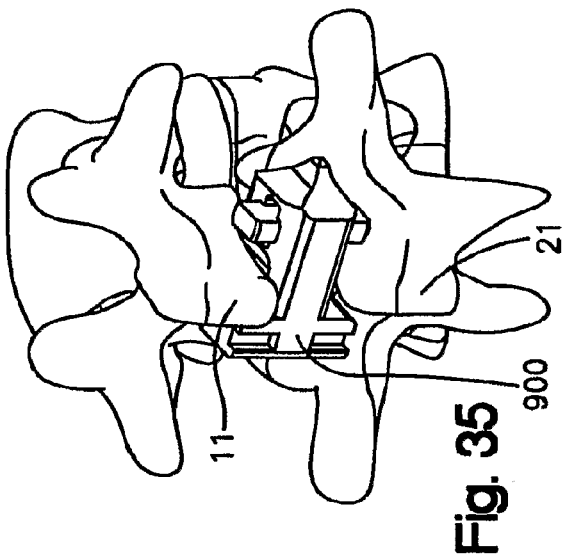
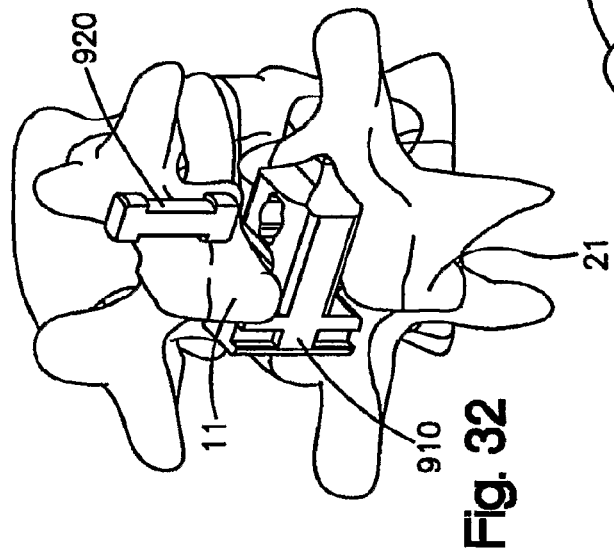
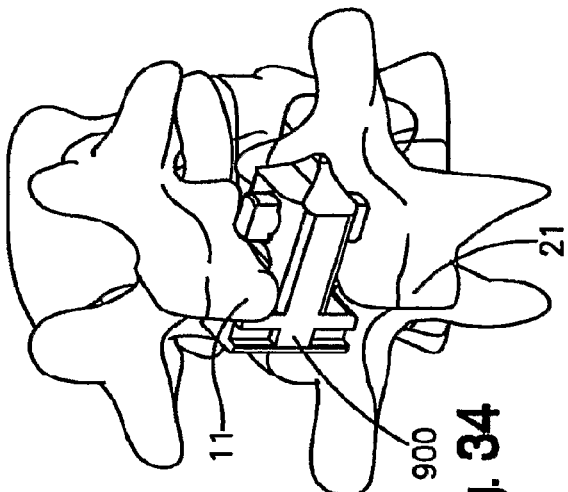

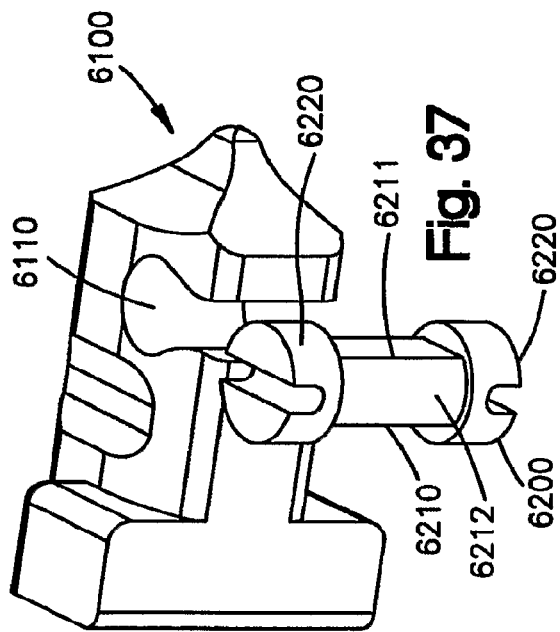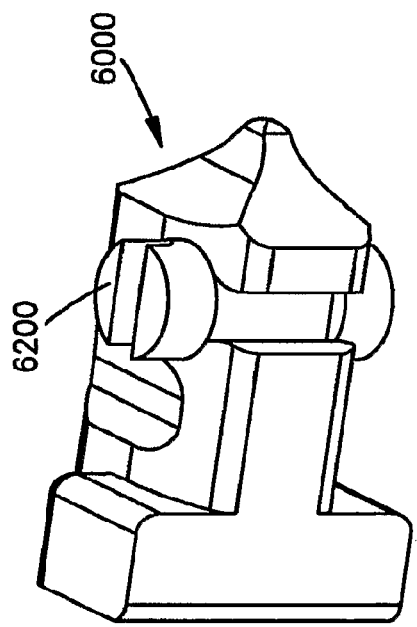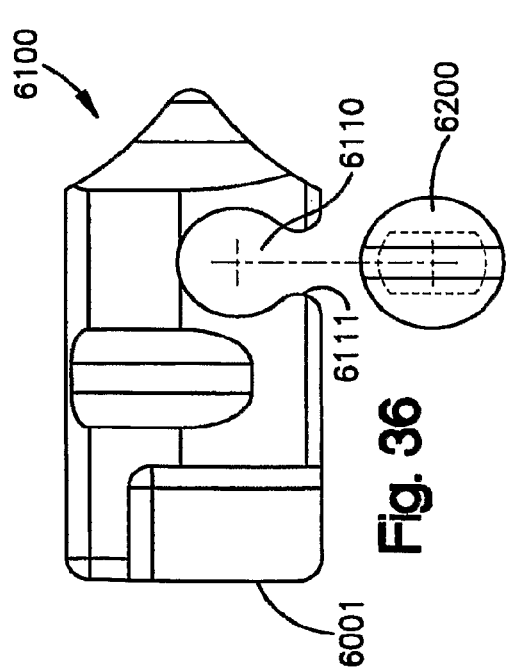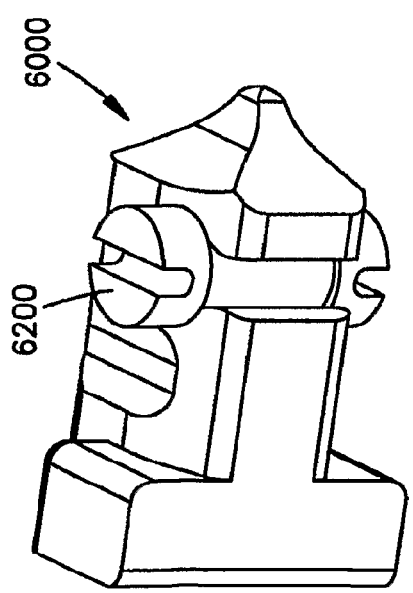

INTERSPINOUS PROCESS SPACER

CROSS-REFERENCE TO RELATED APPLICATIONS

This application claims the benefit of International Application No. PCT/US2007/002791, filed Jan. 31, 2007, entitled "Interspinous Process Spacer." This application also claims the benefit of priority of U.S. Provisional Application Ser. No. 60/764,069, filed Feb. 1, 2006. The entire disclosure of these applications is incorporated herein by reference.

TECHNICAL FIELD OF THE INVENTION

The invention relates to implant for vertebra and spinal applications and more particularly to interspinous process spacers that may be inserted between two vertebrae to replace a damaged or degenerated spinal disc. More particularly, the invention relates to a spacer to be placed between the posterior spinous process of the spine and its method of use.

BACKGROUND OF THE INVENTION

Degenerative disc disease often results in a loss of disc height, which in turn can cause facet and nerve impingement. One standard of care is to remove the disc and fuse the two vertebrae together. However, this can lead to problems at adjacent vertebra levels as those levels become hypermobile to compensate for the loss of mobility at the fused level. A number of devices have therefore been developed to restore height without fusion. Such known devices include artificial discs, pedicle screws with flexible rods, and spacers which may be implanted between spinous processes, referred to herein as interspinous process spacers. Known interspinous process spacers are inserted between the posterior spinous process and can be made of rigid or flexible material. Typically, known interspinous process spacers are placed in the spine in slight distraction to off load the weight of the disc. Interspinous process spacers also typically serve as a stop for extension, and some have attached straps that limit flexion. Many known interspinous spacers are in the shape of an H, wherein the sides of the H prevent the spacer from sliding out from between the processes. Known spacers also are usually made of a metal or a polymer. Ideally, however, bone would be a more suitable material for a spacer, but typical H-shaped bone spacers may result undesirably in the vertebrae fusing to the spacer.

SUMMARY OF THE INVENTION

The present invention provides interspinous process spacers (ISPS), also referred to herein as an a spacer or implant, which may be implanted between spinous processes, for example, to treat patients with spinal stenosis whose symptoms are relieved with flexion.

In one aspect, an interspinous process spacer, or implant, may be inserted laterally into the interspinous space through a small, posterior midline incision, allowing the preservation of the supraspinous ligament. One or more spacers may be placed between spinous processes of adjacent vertebrae, and result in distraction of the spinous processes which may limit extension of the spine. By doing so, implantation of an interspinous process may inhibit or prevent the narrowing of the spinal canal and neural foramen at the level of treatment, thereby relieving pain or other symptoms. Preservation of the supraspinous ligament may provide additional stability, for example by keeping the implant from migrating posteriorly.

BRIEF DESCRIPTION OF THE DRAWINGS

The present invention can be better understood by reference to the following drawings, wherein like references numerals represent like elements. The drawings are merely exemplary to illustrate certain features that may be used singularly or in combination with other features and the invention should not be limited to the embodiments shown.

FIGS. 2-4 are top, front side, and bottom views, respectively, of the interspinous process spacer of FIGS. 1A and 1B;

FIG. 5 is a top view of another illustrative embodiment of an interspinous process spacer according to the invention;

FIG. 11 is a sagittal schematic view of a spine showing a first spacer having horizontally stacked portions and a second spacer having vertically stacked portions;

FIGS. 12 and 13 are end and perspective views, respectively, of another embodiment of a portion of a multi-piece interspinous process spacer;

FIG. 17 is a perspective view of an embodiment of a perforator device;

FIG. 18 is a perspective view of an embodiment of a dilator device;

FIG. 19 is a perspective view of an embodiment of a distractor device;

FIG. 20 is a perspective view of an embodiment of an inserter device;

FIG. 21 is a perspective view of an embodiment of a spacer trial;

FIG. 22 is a perspective view of the inserter device of FIG. 20 holding the trial of FIG. 21;

FIG. 27 is a top view of another embodiment of an interspinous process spacer;

FIG. 28 is a perspective view of an embodiment of a locking pin for use with the interspinous process spacer of FIG. 27;

FIG. 29 is a side view of the interspinous process spacer of FIG. 27;

FIGS. 32-35 are perspective views showing insertion of the interspinous process spacer of FIG. 27 between spinous processes of two vertebrae and locking of the spacer with the pin of FIG. 28;

FIGS. 36 and 37 are top and perspective views, respectively, of another embodiment of an interspinous process spacer and locking pin; and FIGS. 38 and 39 are perspective views of the interspinous process spacer of FIGS. 36 and 37, showing engagement of the locking pin with the body of the interspinous process spacer.

DETAILED DESCRIPTION AND FIGURES

Figure 1A:
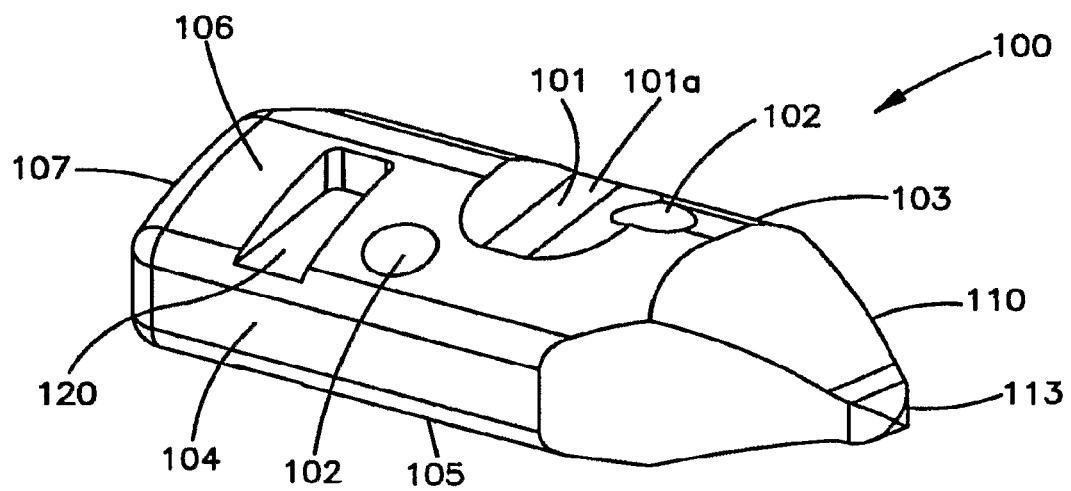
FIG. 1A is a perspective view of a first illustrative embodiment of an interspinous process spacer according to the invention.

FIGS. 1-3 show a first embodiment of an interspinous spacer (100). The spacer (100) may be generally rectangular and have an upper face (106) that generally opposes a lower face (105), front and back sides (104, 103) that generally oppose each other, an end side (107), and a nose (110) that generally opposes the end side (107). The spacer (100) preferably has rounded edges (108) between the upper face (106) and the front (104), end (107), and back sides (103) and between the lower face (105) and the front (104), end (107), and back sides (103). Radiuses of curvature for the rounded edges are each preferably about 1.5 mm. Alternatively, the radiuses can be of other dimensions and do not have to be the same.

The spacer (100) may include one or more depressions (101) extending laterally across the upper (106) and/or lower face (105). Such depressions (101) are preferably dimensioned and shaped to receive a spinous process and may be curved or substantially flat and planar. In one embodiment of the invention, the lower face (105) has a depression (101) having essentially the same dimensions and position as a corresponding depression (101) of the upper face (106). Advantageously, depressions (101) on the upper and/or lower faces (106, 105) may result in reduced, and preferably minimized, bone contact between the spacer (100) and the vertebrae. Such reduced and minimized bone contact may advantageously lower or reduce, if not eliminate, the potential for bone fusion. The upper and/or lower depressions (101) may have any desired radius and/or depth. For example, in one embodiment the depression (101) on the upper face (106) has a radius of curvature of about 6 mm and a depth of about 0.5 mm. Alternatively, the upper and/or lower depression (101) may have other radiuses and depths and can have radiuses and depths different than each other. The one or more depressions (101) may also be positioned as desired. For example, in one embodiment, the center (101a) of the upper depression (101) is positioned at a distance of about 9 mm from the end side. Alternatively, the one or more depressions (1101) may be positioned at other distances from the end side.

The body of the spacer (100) may also include one or more holes (102) as shown in FIG. 1. Such holes (102) preferably extend through the spacer (100), e.g. from the upper face (106) to the lower face (105). The one or more holes (102) may de dimensioned to pass a fixation strap, wire, cord, or the like, for example as described in U.S. Provisional Patent Application No. 60/688,359, filed Jun. 6, 2005 and entitled "Implant for Spinal Stabilization and its Method of Use", which is incorporated by reference herein in its entirety. Alternatively, one or more of the holes (102) may be threaded to accept threaded fixation devices (that may be screwed into position) and the holes (102) may not extend completely through the spacer (100). In one embodiment of the invention, two holes (102) extending through the spacer (100) each have a diameter of about 2.5 mm, and are spaced apart by a center-to-center distance of about 8 nm. Alternatively, the holes (102) can have other center-to-center distances and other diameters, which can be different than each other. In a preferred embodiment, at least one hole (102), e.g. the hole closest to the back side (103) of the spacer (100) as shown in FIG. 2, may pass through the spacer (100) at an oblique angle. Moreover, the spacer (100) alternatively may have other numbers of holes (102) or attachment points, and the holes or attachment points need not be on upper face and/or lower face.

The nose (110) of the spacer (100) may have a generally tapered shape, and extend preferably integrally from the upper face (106), lower face (105), front side (104) and back side (103) of the spacer (100). For example, the nose (110) may taper distally and inwardly to form a generally pointed or rounded distal tip (113). The tapered surfaces may be curved or substantially flat planar surfaces. In a preferred embodiment, the nose (110) is asymmetrical, for example including front edge (112) of the nose and back edge (111) of the nose that have different directions and/or radiuses of curvature. For example, as shown in FIGS. 1-4, the front edge (112) of the nose (e.g., from the front side (104) of the spacer to the tip (113)) may be concave and have a radius of between about 10 mm and about 20 mm, more preferably about 15 mm, while the back edge (111) of the nose (e.g., from the back side (103) of the spacer to the tip (113)) may be convex and have a radius that is about the same as the radius of the front edge of the nose. Alternatively, the radiuses can be of different dimensions and may be different from each other.

In other embodiments, the nose (110) may have a generally symmetrical shape, for example as shown in FIG. 5. In this example, the radiuses of the edges of the nose (110) from the back side (103) to the tip (113) and from the front side (104) to the tip may be between about 10 mm and about 20 mm, more preferably about 14 mm. Alternatively, the radiuses of the nose (110) from the front side (104) to the tip (113) and from the back side (103) to the tip (113) may be of other values and can be different from each other.

In some embodiments, the spacer (100) may include one or more engagement, or interface, features (120). For example, as shown in FIG. 3, the spacer (100) may include an engagement feature (120), also referred to as an inserter interface, to interface with an implant holder device. The engagement feature (120) may include one or more generally planar and opposing recessed surfaces (123, 124), or recesses, in the upper and lower faces (106, 105), for example near the end (107) of the body of the spacer (100). Each recess may be defined by one or more walls, for example an end wall (122), a back wall (125) and a side wall (122), such that each recess is accessible to an implant holder or other device from the front side of the spacer (100). For example, the upper and lower recessed surfaces (123, 124), as shown for example in FIG. 3, may be engaged by opposable jaws of an inserter device (4000) (e.g., as shown in FIG. 20), a forceps, or another device or tool adapted to grip or hold the spacer. In one embodiment, the upper recess of the engagement feature (120) has a height (e.g., distance from the upper face to the recessed surface) of about 3 mm, a depth (e.g., distance from the front side of the spacer to the back wall of the engagement feature) of about 7 mm, and a width (e.g., distance from the end wall to the side wall of the recess) of approximately 4 mm. In this embodiment, the lower engagement feature (120) recess has approximately the same dimensions as the upper engagement feature (120) recess. Alternatively, the engagement feature recesses may have other dimensions, and may be different from each other.

A spacer (100) may have any desired length, width, and thickness. For example, in one embodiment, the length may be between about 20 and 40 mm, more preferably between about 24 and 35 mm. The width and thickness are preferably dimensionally paired and may be variable depending on the spinal application. Preferably, the spacers (100) are provided in a variety of sizes with thickness increasing in any desired increments, e.g., 2 mm increments. Illustrative, representative thicknesses, or height, could be about 6 mm to about 16 mm, for example. The width of the spacer (100) may be paired to the thickness, for example about 4 mm greater than the thickness. Illustrative, representative widths could be about 10 mm to about 20 mm, for example. Alternatively, the spacers (100) may be of other lengths, widths, and thicknesses.

Preferably, the spacers (100) are made from bone, and more preferably from a single piece of cortical or other bone. Cortical bone may reduce and preferably minimizes the possibility of bone fusion. The spacer (100) may be provided with a coating to minimize, resist, or prevent the possibility of bone fusion. In some embodiments, a spacer (100) is made from allograft bone. In other embodiments, autograft bone may be used. Alternatively the spacer (100) may be made of biocompatible materials such as, for example, PEEK, polycarbonate urethane, silicon polycarbonate urethane, or other polymer and plastic materials. The spacer (100) may also be made of metals, such as, for example, titanium or stainless steel, and may also be made of composites, ceramics, or combinations of materials.

Figure 1B:
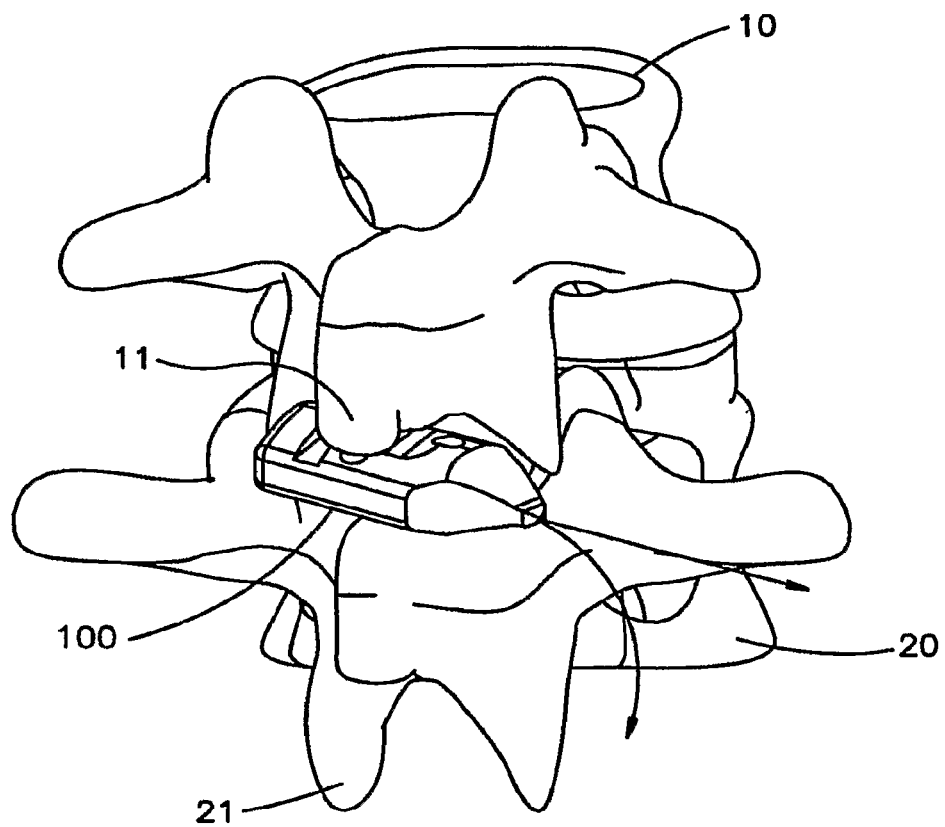
FIG. 1B is a perspective view of the interspinous process spacer of FIG. 1A inserted between the spinous processes of two vertebrae.

As shown in FIG. 1B, a spacer (100) or other implant may be inserted laterally into an interspinous space, for example through a small, posterior midline incision. Such an approach may allow preservation of the supraspinous ligament. One or more spacers (100) may be placed between spinous processes (11, 21) of adjacent vertebrae (10, 20) and result in distraction of the spinous processes (11, 21) which may limit extension of the spine. By doing so, implantation of an interspinous process may inhibit or prevent the narrowing of the spinal canal and neural foramen at the level of treatment, thereby relieving pain or other symptoms. Preservation of the supraspinous ligament may provide additional stability, for example by keeping the implant from migrating posteriorly.

As shown in FIGS. 6-10, a spacer (100) may be fabricated or formed using a number of bone pieces or units. For example, due to a relatively large size of spacer implants (for example, greater than 5 mm in height, more preferably ranging anywhere from 8 to 14 mm or more in height over the depression), it may not be practical to fabricate the spacer from a single piece of bone. When multiple pieces (500), or units, are used to construct an interspinous process spacer (100), it may be preferable to connect the units, for example using one or more connectors or connection features. Such connection features may be fabricated or otherwise integrated within one or more of the units (500).

Figure 6A:
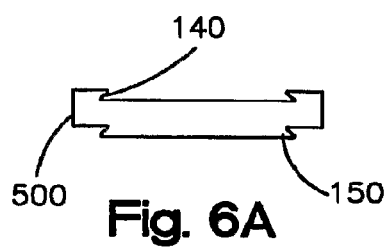
FIGS. 6A and 6B are end and perspective views, respectively, of a portion of a multi-piece interspinous process spacer.
Figure 6B:
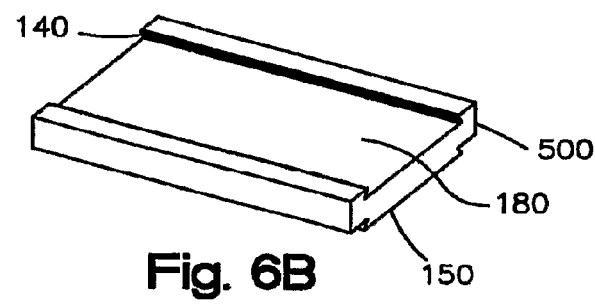

For example one or more of the units (500) may be fabricated to include male and/or female dovetail connections (150, 140) as shown in FIGS. 6A and 6B. Such dovetail connection preferably only permits translation along one direction between mating parts. Once all the pieces (500) are assembled, a hole (160) may be drilled across all of them and a dowel or pin (170), e.g., which may also be made from bone, may be pressed into the hole (160) to secure the assembly. An interference fit between the hole (160) and the pin (170) may hold the entire assembly together. Alternatively the pin (170) can be threaded and may be screwed into the hole (160). The hole (160) may be substantially perpendicular to the surface (180) of the multiple pieces (500) or be angled with respect to the surface (180) of the multiple pieces (500). The angled holes (160) and pins (170) may be oriented in the same, different or opposite directions from one another. One or more additional pins (170) may be used to provide extra stability if desired. Alternatively, cement or adhesive may be used to couple the pieces together. In other embodiments, interspinous process spacers comprise other biocompatible materials instead of or in addition to bone.

Figure 7:
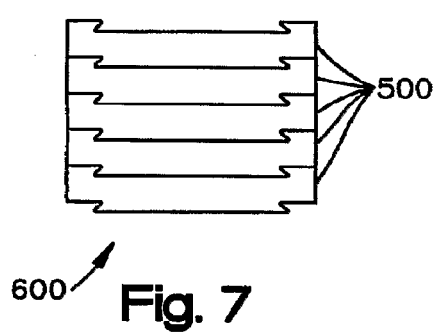
FIGS. 7 and 8 are end and perspective views, respectively, of a multi-piece interspinous process spacer after assembly of the portions of FIGS. 6A and 6B.
Figure 8:
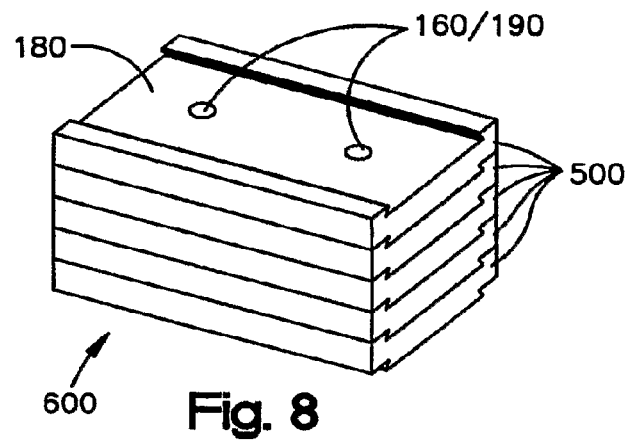
Figure 9:
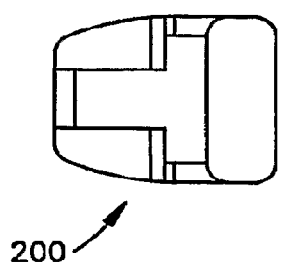
FIGS. 9 and 10 are end and perspective views, respectively, of the multi-piece interspinous process spacer of FIGS. 7 and 8.
Figure 10:
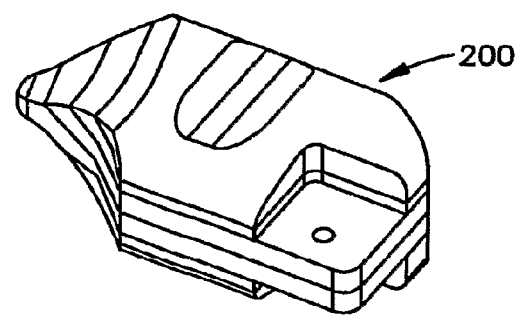

As shown in FIGS. 6A and 6B, a spacer unit (500) may have one male (150) and one female (140) dovetail connection. FIGS. 7 and 8 show a multi-piece (600) construction of stacked units connected (500) using dovetail connections. Such a basic building block, with one male (150) and one female (140) dovetail connection, may be used for the internal layers as shown. For the end pieces, e.g., which form the upper and lower surfaces of the spacer (100), only one connection (male or female) may be needed. The entire assembly (600) may be held together using zero, one, two or more pins (170). Once the multi-piece construction is assembled, it may be treated as one unitary piece. For example, after assembly, other features of the spacer (100) can then be machined into the assembly. FIGS. 9 and 10 show an example of finished interspinous process spacer (200) made from multiple pieces or units (500).

The construction in FIGS. 7 and 8 shows five (500) units of substantially identical thickness. In reality, the number and thickness of the individual pieces could vary. As shown in FIGS. 5 and 6, for example, a basic building block has one male (150) and one female (140) dovetail connection. In reality, each piece (500) could have any number of dovetail connections, male or female. For example, the central piece in the five layer stack may have two female dovetail connections (140). The next two inner pieces could have one male (150) and one female (140) dovetail, and the outer pieces could have one male (150) dovetail. The dovetail connections of the basic building block preferably, although not necessarily run all the way through the part, e.g., a "thru dovetail". However, a blind dovetail (190) as shown in FIGS. 12 and 13, or even tapered dovetail (not shown), may be employed to provide additional resistance between mating parts in at least one direction of translation that a standard thru dovetail does not. FIGS. 9 and 10 show the assembled pieces (500) as horizontal layers (horizontal stacking) in the finished implant (200). The pieces (500) could have been assembled as vertical layers (vertical stacking) (400) instead, e.g. as shown in FIG. 11. If one or more of the individual horizontal layers were actually made from two or more vertically stacked pieces (500), a hybrid combining both horizontal (300) and vertical stacked (400) pieces could be constructed.

Figure 14:
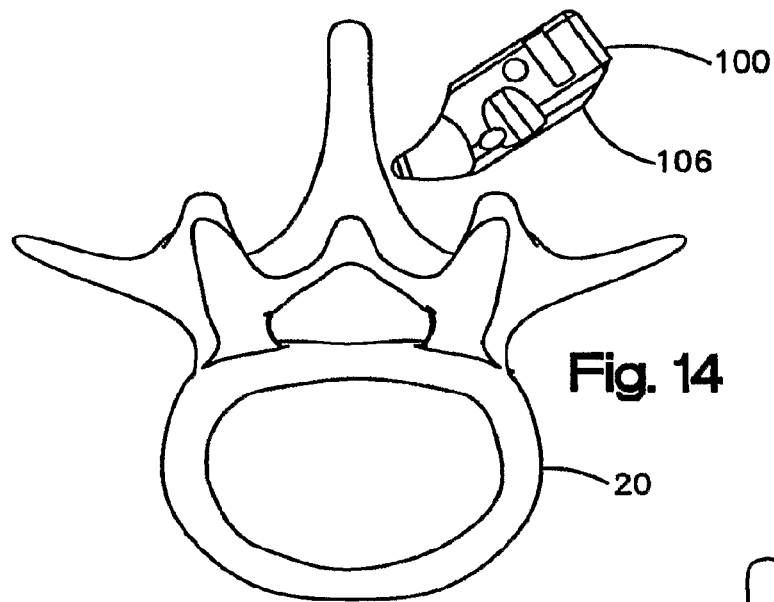
FIGS. 14, 15 and 16 are cranial views of a spine showing lateral insertion of an interspinous process spacer.
Figure 15:
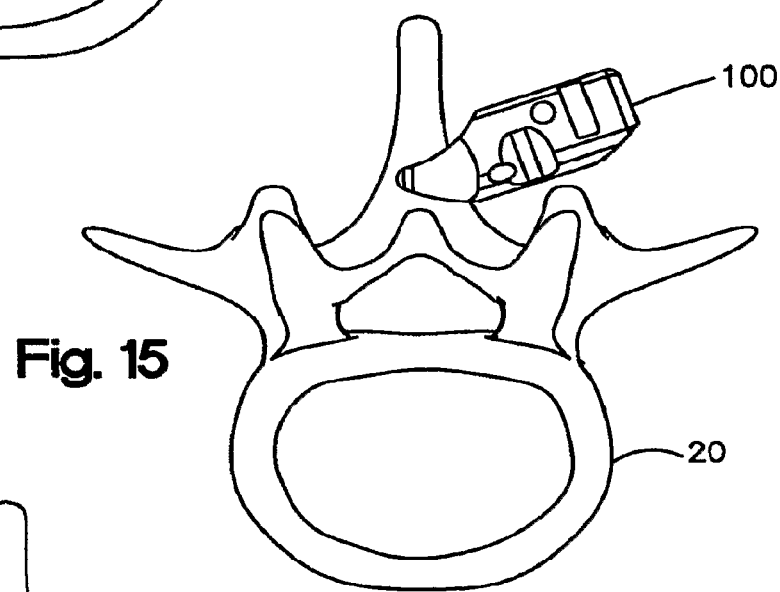
Figure 16:
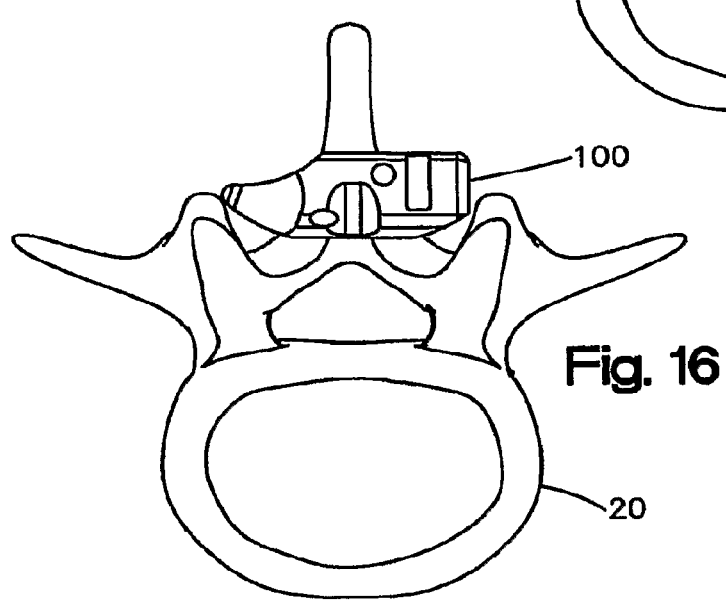

As shown in FIGS. 14-16, the interspinous process spacer (100) is preferably inserted in a curved lateral fashion, for example so as to preserve the supraspinous ligament. The anterior surface (upper face 106) of the spacer (100) may be curved in a similar manner to present a smaller profile to the surrounding tissue upon insertion. For example, it is placed as far anterior as possible to minimize the possibility of posterior migration and dislodgement. The implant (100) may come in different size footprints and heights to adapt to variations in patient anatomy.

One or more of the following instruments may be utilized with an interspinous process spacer (100), e.g., for implanting one or more spacers, and may be included separately, or in a kit or set.

The surgeon may use a perforator, e.g., such as the perforator (1000) shown in FIG. 17 or another suitable tool, to help locate the interspinous space radiographically. After finding the most anterior portion or other desired location of the interspinous space at the level in question, e.g. by determining the position of the perforator tool (1000) or other tool with respect to the spinous processes in a radiographic image, the surgeon may use the sharp tip (1100) of the perforator (1000) to split the interspinous ligament (ISL), while keeping the supraspinous ligament (SSL) intact. Once split, the surgeon may then use the blunt tip (2100) of a dilator (2000), e.g., such as the dilator (2000) shown in FIG. 18 or another suitable tool, to further increase the size of the opening in the ISL.

Next, the surgeon may insert the jaws (3100) of a distractor (3000), e.g., such as the distractor (3000) shown in FIG. 19 or anther suitable tool, into the opening in the ISL such that the opposable jaws (3100) of the distractor (3000) engage the spinous processes (11, 21) of the adjacent vertebrae (10, 20), and distract the spinous processes (11, 21) as much as possible. The open distractor (3000) may be left in place for a desired amount of time, e.g., a few minutes or more, to allow the SSL to stretch out. During this time, the surgeon can assess the mobility of the segment. A scale (3400) on the threaded rod (3200) at the back of the handle (3300) of the distractor (3000) may be used to indicate the amount of interspinous space distraction, e.g., by the amount of distractor jaw (3100) movement.

After removing the distractor (3000), the surgeon may use an inserter (4000), e.g., such as the inserter (4000) shown in FIG. 20 or another suitable tool, to grasp the appropriate sized (100) implant and insert it in the curved lateral fashion described previously. The spacer (100) may be inserted by other means and via different pathways. Alternatively, the surgeon can use an inserter (4000) to grasp an appropriate sized trial (700), e.g., such as that shown in FIGS. 21 and 22, to assess proper implant sizing. Once the proper size has been confirmed, the correct implant size can then be inserted.

Figure 23:
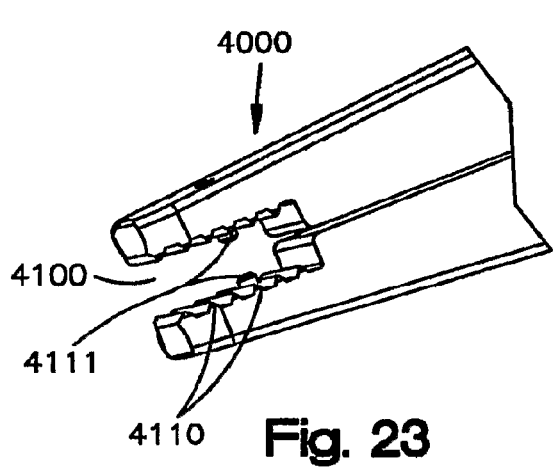
FIG. 23 is a close-up perspective view of another embodiment of an inserter device.
Figure 24:
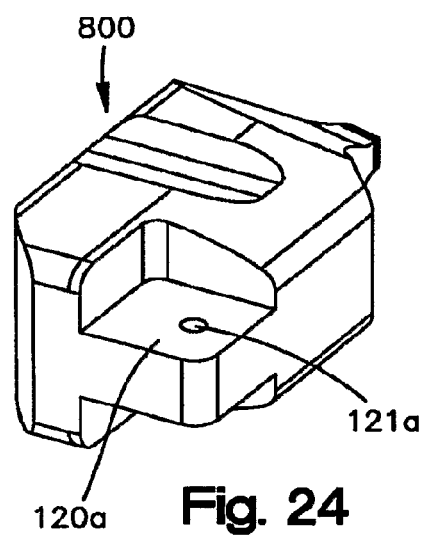
FIG. 24 is a close-up perspective view of another embodiment of a spacer trial.
Figure 25:
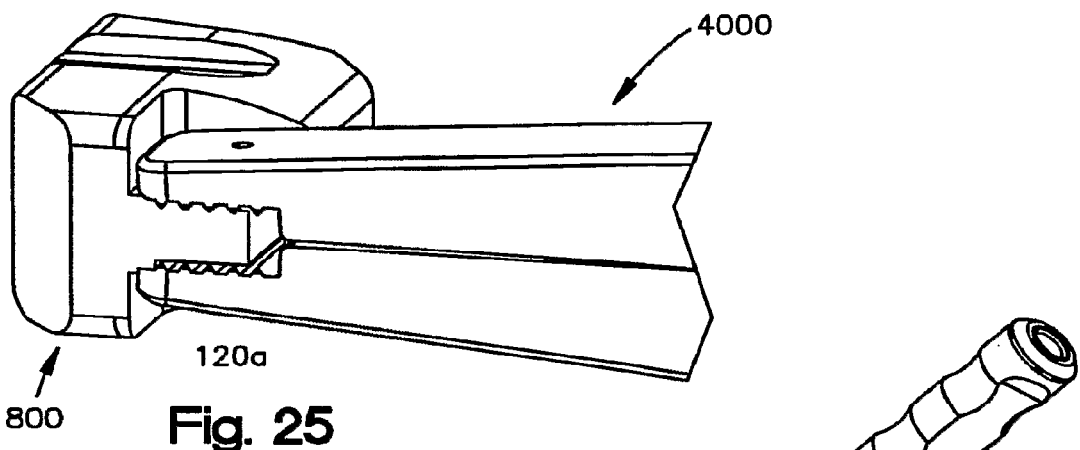
FIG. 25 is a close-up perspective view of the inserter device of FIG. 23 holding the trial of FIG. 24.

FIGS. 23-25 show an example of an alternate inserter interface (4100) and trial (700) adapted to engage with the interface. In this example, the inserter interface (4100) may have a width that is wider, e.g., much wider, than that of above-described embodiments. For example, the inserter interface (4100) may be dimensioned such that the end wall on the alternate trial engagement feature/implant inserter interface (120*a*), e.g., as shown in FIG. 24, is removed. Also, the jaws of the inserter interface (4100) may include engagement pins (4111) which protrude beyond the height of the teeth (4110) as shown in FIG. 23. These pins (4111) are located such that they engage holes (121*a*) placed in the alternate trial/implant insertion interface (120*a*). FIG. 25 shows an example the alternate inserter interface (120*a*) of FIG. 23 engaged with the trial (800) of FIG. 24.

After the appropriate sized implant has been inserted into the interspinous space, the surgeon may use a flexible cord (e.g., a cable, suture, wire, etc.) to secure the implant (100) to one or more of the spinous processes (11, 21). In order to do so, the surgeon may, for example, pass one end of the cord through the ISL of the neighboring interspinous space to access the opposite side.

Figure 26:
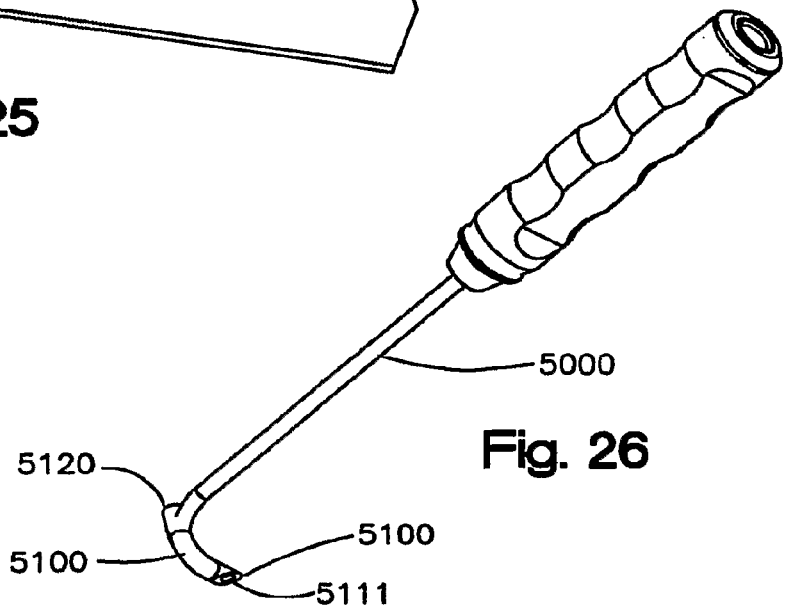
FIG. 26 is a perspective view of an embodiment of a cord passer device.

FIG. 26 shows an embodiment of a cord passer (5000) which may be used to facilitate passing the cord. The bent tube (5100) on the end of the passer may include two openings: the insertion end (5110) and the passing end (5120). The tip (5111) of the passer may be placed on the opposite side of the spinous processes from that of the free end of the flexible cord. The sharp edge on the insertion end (5110) may be used to split the ISL of the neighboring interspinous space. This allows the insertion end (5110) to pass through the ISL onto the same side as the end of the flexible cord while the passing end (5120) remains on the opposite side. The end of the flexible cord may then be fed into the insertion end (5110) opening until it comes out of the opening in the passing end (5120) on the opposite side. Once this is done, the insertion end (5110) may be retracted back to its original side, and the cord passer (5000) can be safely removed.

The approach and technique described above is only one method for inserting an ISPS. A surgeon may choose to use none or only some of the instruments shown, or may chose to use other instruments that may have some of the same or similar features to those described above. For instance, the surgeon may not need to use the dilator (2000) if the opening created by the perforator (1000) is large enough to accommodate the tips (3111) of the distractor (3000). Similarly, the surgeon may choose not to use the perforator (1000) if the tips (3111) on the distractor (3000) are sharp enough to split the ISL at the desired location.

The previously described exemplary technique called for insertion of the trial (700) and/or ISPS after the distractor (3000) had been removed. However, judicious use of a second distractor may permit the insertion of the trial (700) and/or ISPS while this second distractor (3000) remains in place. After reading the maximum interspinous space on its scale indicator (3400), the first distractor (3000) may be removed. A second distractor, for example with a beak width equal to the reading on the scale indicator, may be inserted such that its jaws (3100) are perpendicular to that of the first distractor (3000) (when it was in place). The second distractor may then be actuated to open the ISL further while maintaining the existing interspinous space distraction. With the jaws of the second distractor opened wide enough to accommodate the width of the implant (100), the trial (700) and/or implant (100) can be safely inserted. This simultaneous insertion while distracting the spinous processes could greatly reduce the insertion load needed to insert the implant (100). Once the implant (100) is in place, the second distractor can be carefully removed.

Alternatively, the second distractor could be inserted and actuated with the first distractor (3000) in place. This may require the beak (3110) width of the second distractor to be slightly smaller than the opening between the first distractor jaws (3100). With the jaws of the second distractor opened wide enough to accommodate the ISPS width (e.g., which is equal to or larger than the ISPS height), the jaws (3100) on the first distractor (3000) can be safely closed and removed.

In still another embodiment, a direct posterior insertion approach of the ISPS may be employed as an alternative to a lateral insertion approach. In such a technique, the surgeon may take down the supraspinous ligament and/or the interspinous ligament.

Figure 30:
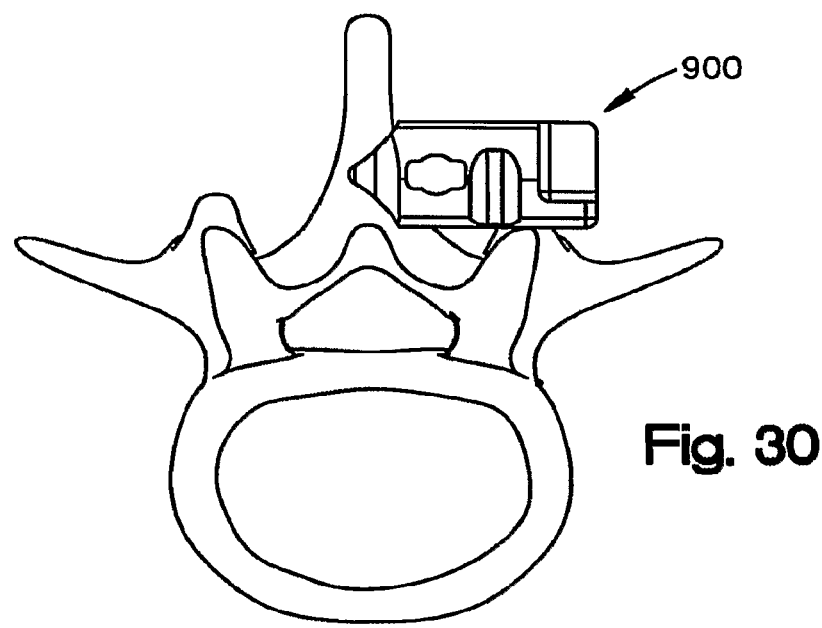
FIGS. 30 and 31 are cranial views of a spine showing lateral insertion of the interspinous process spacer of FIG. 27.
Figure 31:
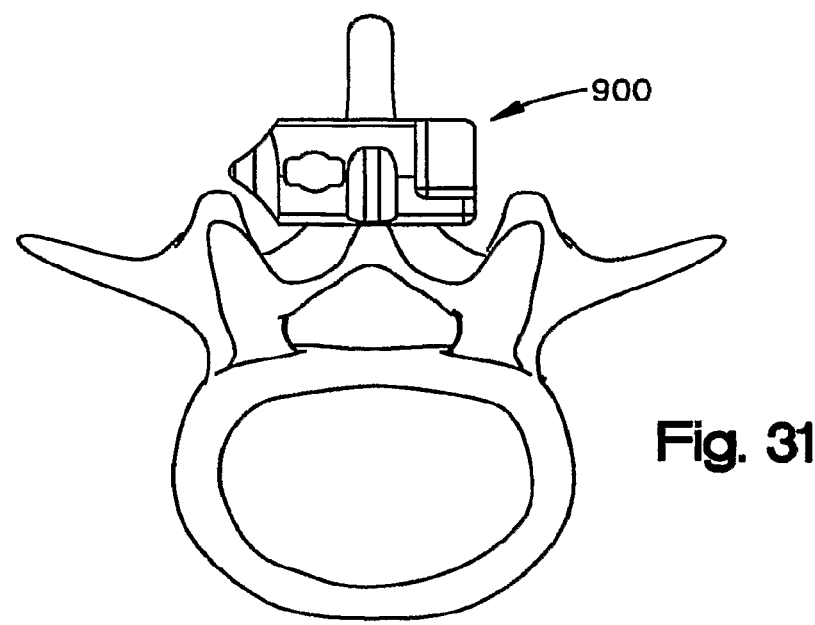

Many variations to the implant design are possible. Although the preferred embodiment uses holes for flexible attachment means, such may not be necessary. For example, FIGS. 27-31 show an alternative implant (900), or stand-alone device, made from multiple components. As shown in FIGS. 27 and 29, the main body (910) in this example may have a tip or nose (911) that is more symmetrical (e.g., rather than curved as shown in above-described embodiments). Such symmetrical configuration may permit, for example, a more direct lateral insertion as shown in FIGS. 30-31. The opposite end of the spacer (900) may include a high wall (912) protruding from the top (916) and bottom (917) surfaces of the main body (910). This high wall (912) is preferably large enough to engage the lateral surface of the spinous process above and below the body. In between the tip (911) and depression (913), a hole (914*a*) and slot (914*b*) configuration may run through the body. The hole and slot configuration (914) is preferably sized to permit the insertion of a locking pin (920).

FIG. 28 shows an exemplary locking pin (920). The locking pin (920) may have two heads (921a, 921b) and a cylindrical midsection (922). The heads (921a, 921b) are preferably sized to slide through the slots (914b) in the main body (910) of the spacer (900). The cylindrical midsection (922) is preferably also sized to slide through the hole (914a) in the main body (910). The locking pin (920) preferably has a length which is the same or similar to the length of the high wall (912) on the main body (910).

After the main body (910) has been inserted between the spinous processes (11, 21), the locking pin (920) may be assembled, for example as shown in FIGS. 32-35. The locking pin (920) is oriented so that it can be inserted into the hole and slot configuration (914) in the main body, for example using an insertion tool, forceps, or other device (not shown). Once the lower head (921b) of the locking pin (920) reappears on the opposite side of the main body (910) of the spacer (900) as shown in FIG. 34, the entire locking pin (920) may be rotated, e.g., approximately 90 degrees as shown in FIG. 35, for example such that the upper head (921a) extends above the main body (910) of the spacer (900) and the lower head (921b) extends below the main body (910). The upper and lower heads (921a, 921b) on the locking pin (920) are preferably tall enough to engage the lateral surface of the spinous process above and below the body when locked as shown in FIG. 35, capturing the spinous processes (11, 21) between the locking pin (920) and high wall (912) of the main body (910) of the spacer (900). Alternatively, the heads (921 a, 921b) of the locking pin (920) may rotate with respect to the midsection, and may be rotated, e.g., using a forceps or other tool after insertion to lock the pin.

FIGS. 36-39 show another embodiment (6000) using a slightly different locking pin (6200) mechanism. In this example, instead of inserting the locking pin (6200) from above or below, a locking pin (6200) is inserted into the hole (6110) from the side, e.g., through a slot (6111) in the front side of the hole (6110) as shown in FIG. 36. The midsection (6210) of the pin (6200) preferably has one or more flat sides (6211) and one or more rounded sides (6212) as shown in FIG. 37. The midsection of the pin may be thinner between the flat surfaces (6211) so that it can slide through the slot (6111) and into the larger hole (6110 in the spacer implant (6000), and thicker between the rounded sides (6212) so that once the pin (6200) is located in the hole (6110) and rotated, e.g., approximately 90° the pin (6200) can not slide out of the slot (6111). The enlarged head areas (6220) are sized to hold the implant (6000) between the spinous process in conjunction with the raised walls (6120) on the back end (6001) of the implant.

In other embodiments, the locking pin may be a threaded pin, while the hole and slot configuration may be replaced a corresponding by a threaded hole. The high wall on the main body could also be replaced by another locking pin. The slot in the hole and slot configuration could permit the addition of flexible attachment methods (e.g., a cable, suture, wire, etc.). The flexible attachment cord may provide interference with the locking pin, insuring it did not disassemble from the main body. Interspinous process spacers with various combinations of the features previously described above are envisioned.

Having a large mismatch in mechanical properties between implant and surrounding bone can often lead to resorption of the surrounding bone. One of the advantages of making the interspinous process spacer from bone is that its mechanical properties may be similar to that of the surrounding bone and thus minimize the likelihood of this occurring. Other materials, like PEEK for example, that have mechanical properties similar to bone could also be used. In other embodiments, other common implantable materials like titanium, stainless steel, ceramics, and composites could also be used.

The application of this implant design and insertion method is not limited the lumbar spine as shown, but could easily be adapted for other areas of the spine or other joints or body parts.

While it is apparent that the illustrative embodiments of the invention disclosed herein fulfill the objectives stated above, it will be appreciated that numerous modifications and other embodiments may be devised by those skilled in the art. Features and structures, such as, for example, the size, shape, and location of the spacer depressions can be used singularly or in combination with other features and structures. Therefore, it will be understood that the appended claims are intended to cover all such modifications and embodiments which come within the spirit and scope of the invention.

Many modifications and variations of this invention can be made without departing from its spirit and scope, as will be apparent to those skilled in the art. In particular, it will be clear to those skilled in the art that the invention may be embodied in other specific forms, structures, arrangements, proportions, and with other elements, materials, and components, without departing from the spirit or essential characteristics thereof. The specific embodiments described herein are offered by way of example only, and the invention is to be limited only by the terms of the appended claims, along with the full scope of equivalents to which such claims are entitled.

We claim:

1. An interspinous spacer for implantation between spinous processes of the spine, the spacer comprising:
 a main body having a first face, a second face, a front side, a back side, a leading edge and a trailing edge,
 the first face for contacting a first spinous process and the second face for contacting a second spinous process,
 the leading edge further comprising, a first edge having a convex curvature and a second edge generally opposing the first edge and having a concave curvature,
 wherein the front side and back side are spaced apart and extend between the first face and second face, and
 wherein the front side extends directly and continuously from the trailing edge to the first edge and the back side extends directly and continuously from the trailing edge to the second edge, and
 wherein the first edge and second edge taper distally, and inwardly, with a continuously shrinking distance between the first edge and the second edge along the concave and convex curvatures until reaching a generally pointed or rounded distal tip, and wherein the spacer is configured for lateral insertion between the first and second spinous processes via the leading edge,
 wherein the body further comprises an interface for engaging engage with a tool for inserting the spacer, the interface comprising a recessed surface in at least one of the first face and the second face, the recessed surface having an opening on the front side.

2. The spacer of claim 1, wherein the first face includes a first depression and the second face comprises a second depression for receiving the first and second spinous processes, respectively.

3. The spacer of claim 1, wherein the main body comprises bone.

4. The spacer of claim 3, wherein the main body comprises a single piece of bone.

5. The spacer of claim 3, further comprising a first depression located between a pair of holes on the first face, the holes extending through the main body from the first face to the second face and configured to receive a flexible fixation strap for securing the spacer to at least one of the spinous processes.

6. The spacer of claim 5, further comprising a second depression on the second face, wherein the pair of holes are located to one side of the second depression on the second face.

7. The spacer of claim 1, wherein the first edge has a radius of curvature that is greater than a radius of curvature of the second edge.

8. The spacer of claim 1, further comprising:
at least one wall extending from at least the first face of the main body and located towards an opposite end of the main body from the leading edge; and
a hole extending through the main body from the first face to the second face, the hole positioned on the main body between the leading edge and the wall and configured to receive a pin for locking the spacer between the spinous processes.

9. The spacer of claim 1, further comprising a first nose surface extending from the first face and a second nose surface extending from the second face.

10. The spacer of claim 9, wherein the first and second nose surfaces taper distally, and inwardly, with a continuously shrinking distance until reaching the generally pointed or rounded distal tip.

11. The spacer of claim 10, wherein the first face extends directly and continuously from the trailing edge to the first nose surface and the second face extends directly and continuously from the trailing edge to the second nose surface.

12. The spacer of claim 11, wherein the nose surfaces extend between the first and second edges.

13. The spacer of claim 1, wherein the front side has a planar surface and the back side has a planar surface parallel to the planar surface of the front side.

14. The spacer of claim 1, further comprising rounded edges between the first face, front side and trailing edge.

15. The spacer of claim 14, further comprising rounded edges between the second face, back side and trailing edge.

16. The spacer of claim 1, wherein the spacer has only a single distal tip.

17. An interspinous spacer for implantation between spinous processes of the spine, the spacer comprising:
a main body having a first face, a second face, a front side, a back side, a leading edge and a trailing edge,
the first face for contacting contact a first spinous process and the second face for contacting contact a second spinous process,
a first depression located between a pair of holes on the first face, the pair of holes extending through the main body from the first face to the second face, the first depression sized and configured to receive a flexible fixation strap for securing the spacer to at least one of the spinous processes,
a second depression on the second face, wherein the pair of holes are located to one side of the second depression on the second face,
the leading edge further comprising, a first edge having a convex curvature and a second edge generally opposing the first edge and having a concave curvature,
wherein the front side and back side are spaced apart and extend between the first face and back face, and
wherein the front side extends directly and continuously from the trailing edge to the first edge and the back side extends directly and continuously from the trailing edge to the second edge, and
wherein the first edge and second edge taper distally, and inwardly, with a continuously shrinking distance between the first edge and the second edge along the concave and convex curvatures until reaching a generally pointed or rounded distal tip, and wherein the spacer is configured for lateral insertion between the first and second spinous processes via the leading edge.

18. An interspinous spacer for implantation between spinous processes of the spine, the spacer comprising:
a main body having a first face, a second face, a front side, a back side, a leading edge and a trailing edge,
the first face for contacting contact a first spinous process and the second face for contacting contact a second spinous process,
the leading edge further comprising, a first edge having a convex curvature and a second edge generally opposing the first edge and having a concave curvature,
wherein the front side and back side are spaced apart and extend between the first face and back face, and
wherein the front side extends directly and continuously from the trailing edge to the first edge and the back side extends directly and continuously from the trailing edge to the second edge, and
wherein the first edge and second edge taper distally, and inwardly, with a continuously shrinking distance between the first edge and the second edge along the concave and convex curvatures until reaching a generally pointed or rounded distal tip, and wherein the spacer is configured for lateral insertion between the first and second spinous processes via the leading edge;
wherein the main body comprises bone.

* * * * *